United States Patent
Scetbon

(12) 
(10) Patent No.: US 6,478,727 B2
(45) Date of Patent: *Nov. 12, 2002

(54) PERCUTANEOUS DEVICE AND METHOD FOR TREATING URINARY STRESS INCONTINENCE IN WOMEN USING A SUB-URETHRAL TAPE

(75) Inventor: Victor Scetbon, Paris (FR)

(73) Assignee: Sofradim Production, Trevoux (FR)

( * ) Notice: Subject to any disclaimer, the term of this patent is extended or adjusted under 35 U.S.C. 154(b) by 26 days.

This patent is subject to a terminal disclaimer.

(21) Appl. No.: 09/765,351

(22) Filed: Jan. 22, 2001

(65) Prior Publication Data

US 2001/0018549 A1 Aug. 30, 2001

Related U.S. Application Data

(63) Continuation-in-part of application No. 09/489,336, filed on Jan. 21, 2000, now Pat. No. 6,406,423.

(30) Foreign Application Priority Data

Oct. 5, 2000 (FR) .............................................. 00 12753

(51) Int. Cl.[7] .......................... A61F 2/02; A61B 17/04; A61B 17/32

(52) U.S. Cl. .......................... 600/30; 606/148; 606/167

(58) Field of Search .......................... 600/30; 128/898; 606/41, 148, 167

(56) References Cited

U.S. PATENT DOCUMENTS 5,112,344 A * 5/1992 Petros ......................... 606/148
5,836,314 A * 11/1998 Benderev et al. ........... 128/898
5,899,909 A    5/1999 Claren et al.

(List continued on next page.)

OTHER PUBLICATIONS

Petros, P.E.P. and Ulmsten, U.I. An integral theory and its method for the diagnosis and management of female urinary incontinence. *Scand J Urol Nephrol Suppl.* 1993; 153: 1–93. PMID: 8108659.

(List continued on next page.)

*Primary Examiner*—Eric F. Winakur
*Assistant Examiner*—Nikita R Veniaminov
(74) *Attorney, Agent, or Firm*—Oliff & Berridge, PLC

(57) ABSTRACT

A device for treating urinary stress incontinence in women includes a flexible and elongate mechanism including a tape for supporting a urethra and a flat protective sheath enveloping the tape; and a puncturing needle with an active distal end and a proximal end connected to a first end of the flexible and elongate mechanism, wherein the proximal end of the puncturing needle is connected to a first end of the flexible and elongate mechanism by an intermediate traction element, a second end of the flexible and elongate mechanism being free. A method for treating urinary stress incontinence in a woman suffering from urinary stress incontinence is also provided including (a) forming an opening in an anterior vaginal wall; (b) creating, from two small suprapubic incisions formed in the abdominal wall, a right track and a left track from the abdominal skin to the opening formed in the anterior vaginal wall; (c) using a needle and an intermediate traction element to follow one of the tracks and following the other track with at least a needle; (d) verifying by cystoscopy that the paths of the tracks are outside the bladder and the urethra; (e) using a support tape surrounded by a plastic sheath to follow the tracks by passage under an inferior surface of the urethra; (f) adjusting a loop formed by the sheathed tape under the inferior surface of the urethra; (g) removing the sheath by pulling the sheath toward the outside of the woman's body through the small suprapubic incisions; and (h) leaving the tape implanted from the first to the second incision and around the urethra to support the urethra.

27 Claims, 8 Drawing Sheets

U.S. PATENT DOCUMENTS

| | | | | |
|---|---|---|---|---|
| 6,056,688 A | * | 5/2000 | Benderev et al. | 128/898 |
| 6,091,995 A | * | 7/2000 | Ingle et al. | 606/41 |
| 6,099,547 A | * | 8/2000 | Gellman et al. | 606/167 |
| 6,273,852 B1 | | 8/2001 | Lehe et al. | |

OTHER PUBLICATIONS

Ulmsten, U., Henriksson, L., Johnson, P. and Varhos, G. An ambulatory surgical procedure under local anesthesia for treatment of female urinary incontinence. *Int Urogynecol J Pelvic Floor Dysfunct.* 1996; 7(2): 81–86. PMID: 8798092.

Falconer, C., Ekman–Ordeberg, G., Malmstrom, A. and Ulmsten, U. Clinical outcome and changes in connective tissue metabolism after intravaginal slingplasty in stress incontinent women. *Int Urogynecol J Pelvic Floor Dysfunct.* 1996; 7(3): 133–7. PMID: 8913830.

Ulmsten, U. Some reflections and hypotheses on the pathophysiology of female urinary incontinence. *Acta Obstet Gynecol Scand.* 1997; Suppl. 166(76); 3–8.

Petros, P.E.P. and Ulmsten, U.I. Non stress non urge female urinary incontinence—diagnosis and cure: a preliminary report. *Acta Obstet Gynecol Scand.* 1990; 69: Suppl. 153: 69–70.

DeLancey, J.O.L. Structural support of the urethra as it relates to stress urinary incontinence: the hammock hypothesis. *Am J Obstet Gynecol.* 1994; 170: 1713–20.

Bailey, K.V. A clinical investigation into uterine prolapse with stress incontinence: treatment by modified Manchester colporrhaphy part II. *J Obstet Gynaecol Br Emp.* 1956; 63: 663–76.

Greenwald, S.W., Thornbury, J.R. and Dunn, L.J. Cystourethrography as a diagnostic aid in stress incontinence. *Obstet Gynecol.* 1967; 29: 324–7.

Faysal, M.H., Constantinou, C.E., Rother, L.F. and Govan, D.E. The impact of bladder neck suspension on the resting and stress urethral pressure profile: a prospective study comparing controls with incontinent patients preoperatively and postoperatively. *J Urol Neurol Urodyn.* 1981; 125: 55–60.

Wang, A.C. and Lo, T.S. Tension–free vaginal tape. A minimally invasive solution to stress urinary incontinence in women. *The Journal of Reproductive Medicine.* 1998; 43(5): 429–434.

Hilton, P. A clinical and urodynamic study comparing the Stamey bladder neck suspension and suburethral sling procedures in the treatment of genuine stress incontinence. *Br J Obstet Gynecol.* 1989; 96: 213–220.

Hilton, P. and Stanton, S.L. A clinical and urodynamic assessment of the Burch colposuspension for genuine stress incontinence. *Br J Obstet Gynecol.* 1983; 90: 934–939.

Ulmsten, U. and Petros, P. Intravaginal slingplasty (IVS): An ambulatory surgical procedure for treatment of female urinary incontinence. *Scan J Urol Nephrol.* 1995; 29: 75–82.

Hilton, P. The role of urodynamics in pelvic floor re–education. *Pelvic Floor Re–education: Principles and Practice.* London. Springer–Verlag. 1994; 51–63.

McGuire, E.J. and Lytton, B. Pubovaginal sling procedure for stress incontinence. *J Urol.* 1978; 119: 82–84.

Blaivas, J.G. and Jacobs, B.Z. Pubovaginal fascial slng for the treatment of complicated stress urinary incontinence. *J Urol.* 1991; 145: 1214–1218.

Muller, S.C., Steinbach, F., Maurer, F.M., Melchior, S.W., Stein, R. and Hohenfellner, R. Long–term results of fascial sling procedure. *Int Urogyn J.* 1993; 4: 199–203.

Henriksson, L. and Ulmsten, U. A urodynamic evaluation of the effects of abdominal urethrocystopexy and vaginal sling urethroplasty in women with stress incontinence. *Am J Obstet Gynecol.* 1978; 131: 77–82.

\* cited by examiner

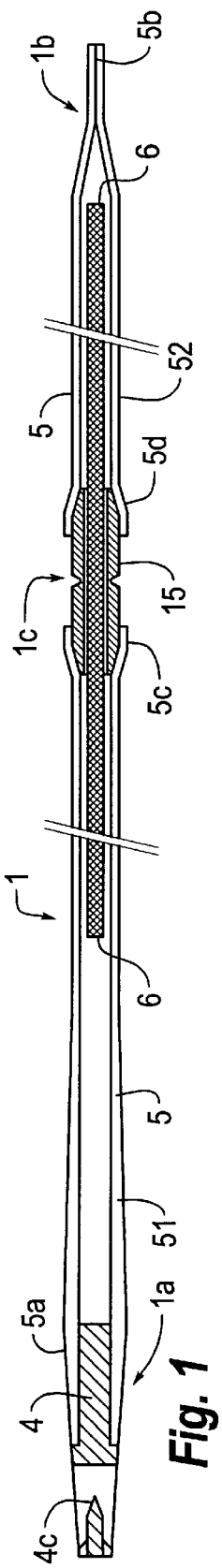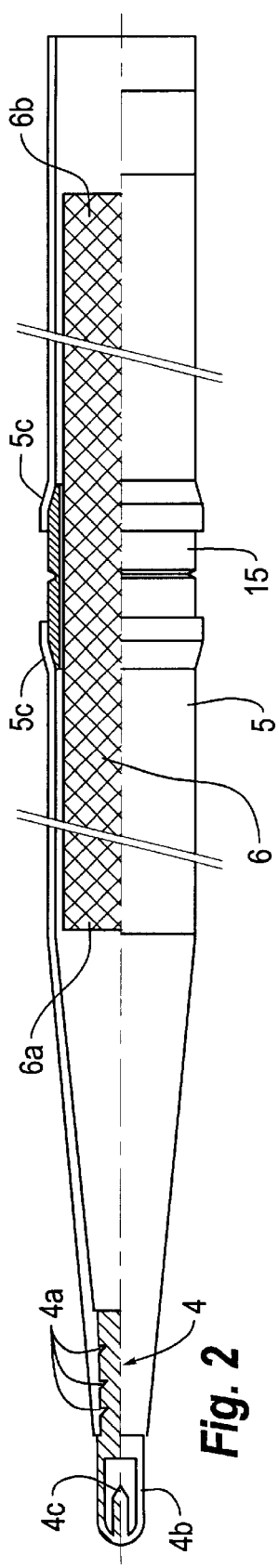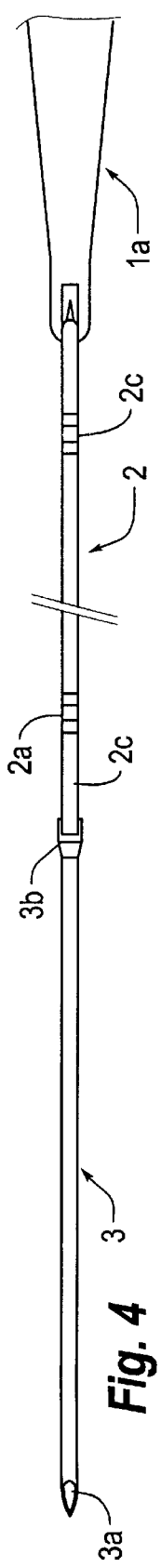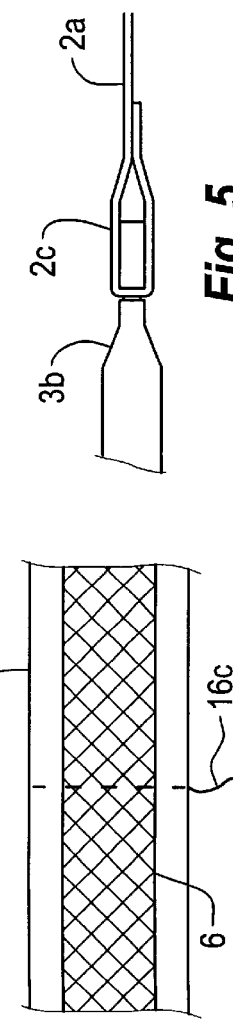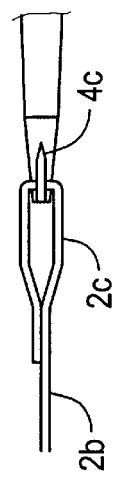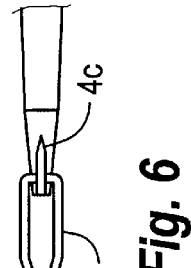

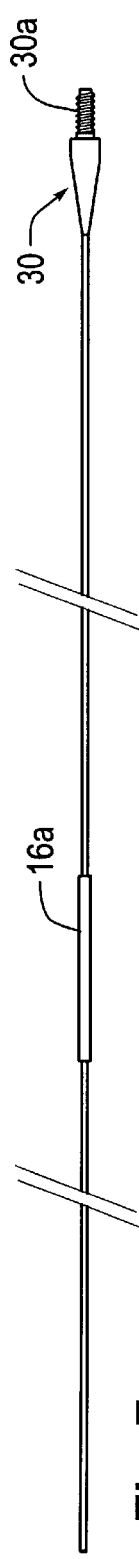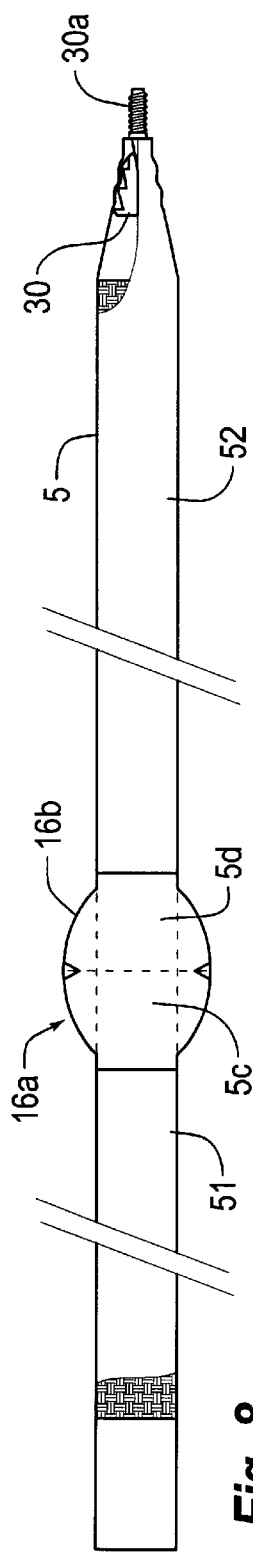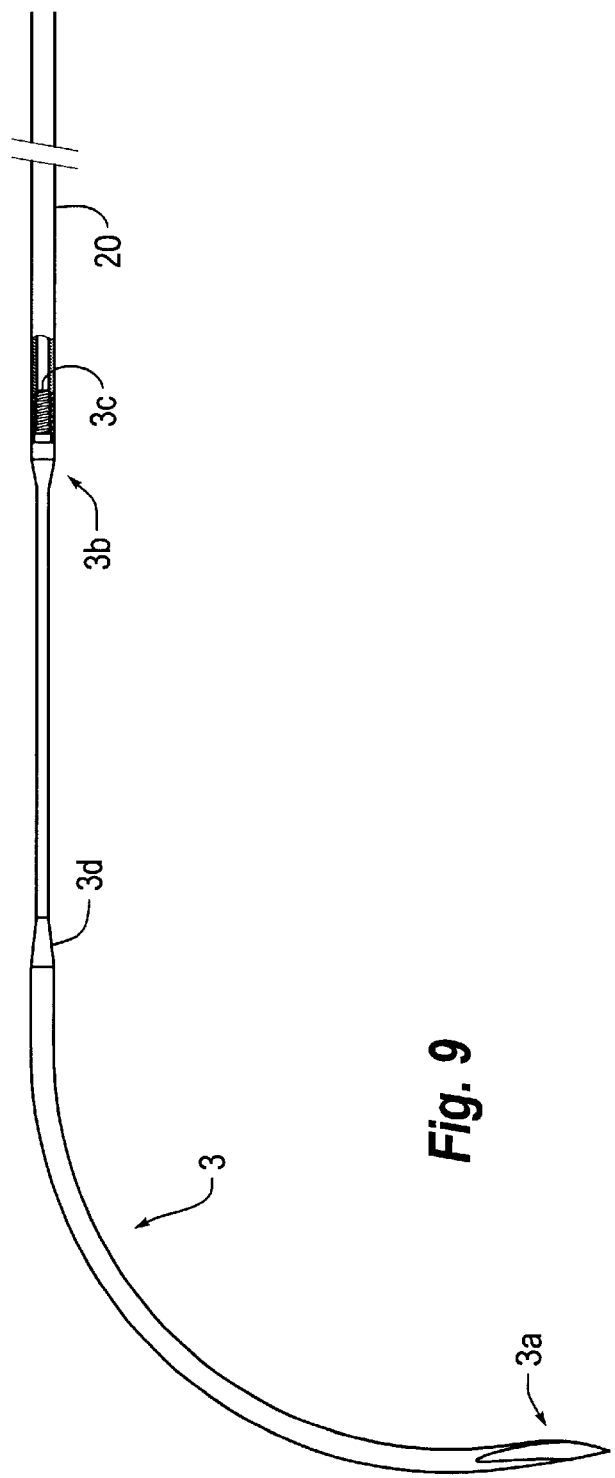
Fig. 7
Fig. 8
Fig. 9

PERCUTANEOUS DEVICE AND METHOD FOR TREATING URINARY STRESS INCONTINENCE IN WOMEN USING A SUB-URETHRAL TAPE

This is a Continuation-in-Part of application Ser. No. 09/489,336 filed Jan. 21, 2000, now U.S. Pat. No. 6,406,423. The entire disclosure of the prior application is hereby incorporated by reference herein in its entirety.

BACKGROUND OF THE INVENTION

1. Field of Invention

The present invention relates to the problems of urinary incontinence in women and more specifically to the problems of urinary stress incontinence. The invention relates more particularly to a percutaneous device for treating urinary stress incontinence in women using a sub-urethral tape.

2. Description of Related Art

These problems are currently treated during surgical interventions under local, regional or general anesthetic and consist in implanting a tape in such a way as to support the urethra without tension.

Thanks to the regional or local anesthesia, the surgeon can immediately check that continence has been restored, with the participation of the patient.

An intervention such as this is performed using an appropriate device including special instruments.

In particular, it is a known practice in treating urinary incontinence to use a tape that can be implanted under the urethral canal, and a sheath surrounding the tape, where the sheath is withdrawn from the tape after the latter has been implanted.

There is a known device for treating urinary stress incontinence in women, comprising:
- a flexible and elongate urethra support means comprising a tape and a protective sheath lying flat and enveloping the tape, and
- a puncturing needle with an active distal end and a proximal end connected to a first end of the flexible and elongate urethra support means.

Thus, U.S. Pat. No. 5,899,909 discloses a treatment method and a treatment device for incontinence. The device described, which allows a tape to be placed under the urethra, comprises two special needles. These are mounted in turn, by screw fastening, on a reusable steel insertion tool made of a handle and of a threaded manipulator rod which allows each of the needles to be manipulated in turn. Each needle is fixed to one of the ends of the tape-sheath assembly.

Each end of the tape-sheath assembly is fixed to a frustoconical part of one end of the corresponding needle, using a shrunk or bonded polymer ring.

The tape is therefore implanted by introducing each of the needles through a short incision in the anterior vaginal wall, these incisions being one on each side of the central position of the urethra.

The needles implanted in turn using the manipulator rod, then travel up around the bladder and the pubic bone and reemerge from the body through incisions made in the abdominal wall in the suprapubic region.

The two halves of the sheath which overlap at the middle of the tape are withdrawn by pulling on the ends that emerge from the suprapubic incisions.

A device such as this requires the use of ancillaries of the insertion handle and rigid intravesical catheter guide types especially designed for this type of surgical intervention.

The known surgical intervention also has a disadvantage insofar as the needles are introduced into the anterior wall of the vagina to reemerge in the suprapubic region. This bottom-upward path cannot be controlled precisely for going around the base of the bladder. Vesical perforations are far from uncommon. They need to be recognized preoperatively through the use of two cystoscopies and entail repeating the maneuvers under more difficult conditions.

The two accessories (manipulator handle and rigid probe guide) must therefore be available to the surgical team during each intervention, having been previously washed, packaged and sterilized prior to each use. In addition, this lateral passage with respect to the bladder, with a vaginal point of entry runs the risk that the point of the needle will injure the iliac vessels in the retrocrural region. These vascular lesions have been observed and have led to fatalities.

Another drawback of the known device lies in the difficulty of repeating the intervention, using the same device, when cystoscopy reveals that the sheath-tape assembly has taken the wrong course. Retreat may prove difficult and tricky for the sheath, and especially for the bulky needles.

The sheath-tape assembly has therefore to be cut and the device can no longer be used to take a different path. It also carries the risk of no longer being sterile as it may have been contaminated during these additional maneuvers.

Thus no percutaneous treatment exists for female urinary stress incontinence which uses a tape which can lead to the devices and technique of the present invention.

SUMMARY OF THE INVENTION

The present invention provides a device for treating urinary stress incontinence in women comprising a flexible and elongate mechanism comprising a tape for supporting a urethra and a flat protective sheath enveloping the tape; and a puncturing needle with an active distal end and a proximal end connected to a first end of the flexible and elongate mechanism, wherein the proximal end of the puncturing needle is connected to a first end of the flexible and elongate mechanism by an intermediate traction element, a second end of the flexible and elongate mechanism being free.

A method for treating urinary stress incontinence in a woman suffering from urinary stress incontinence is also provided by the present invention comprising (a) forming an opening in an anterior vaginal wall; (b) creating, from two small suprapubic incisions formed in the abdominal wall, a right track and a left track from the abdominal skin to the opening formed in the anterior vaginal wall; (c) using a needle and an intermediate traction element to follow one of the tracks and following the other track with at least a needle; (d) verifying by cystoscopy that the paths of the tracks are outside the bladder and the urethra; (e) using a support tape surrounded by a plastic sheath to follow the tracks by passage under an inferior surface of the urethra; (f) adjusting a loop formed by the sheathed tape under the inferior surface of the urethra; (g) removing the sheath by pulling the sheath toward the outside of the woman's body through the small suprapubic incisions; and (h) leaving the tape implanted from the first to the second incision and around the urethra to support the urethra.

The object of the present invention is to overcome the drawbacks of the prior art so as to obtain a different operative technique which is easier, quicker and safer (as far as the bladder and vessels are concerned). The risk of vascular lesion is minimised because of the orientation and the given direction of the needle from the start of the procedure. The risk of vesical puncture is small even in the case of previous interventions in this regard, as is particularly frequent in this type of pathology. Using the device and operating method of the invention, the percutaneous route is used to form top-to-bottom tracks using the needle, i.e., penetrating via abdominal cutaneous mini-incisions to exit via a previously formed vaginal opening. Detachment of the vagina allows the index finger of the surgeon to be insinuated up to the lower rim of the pubis and thus enables the track of the needle to be precisely directed.

The device of the invention enables tracks to be made from top to bottom on both sides of the abdomen and enables the absence of vesical puncturing to be confirmed by cystoscopy before engaging the sheath-tape system. The present device makes it possible to employ the techniques that will be described in detail later on in this description.

Another object of the present invention is to produce a device for treating urinary incontinence which can be reused easily if it is introduced into the body in a non-optimum path, an eventuality which, according to the present invention, can occur only under exceptional circumstances if there is very strong adhesion between the bladder and the pubis, generally as the result of earlier interventions.

According to an embodiment of the invention, the proximal end of the puncturing needle is connected to the first end of the flexible means by virtue of an intermediate traction element, the second end of the flexible means being free or extended by an additional intermediate traction element.

According to one embodiment of the device according to the invention, the protective sheath completely envelopes the tape, including its first and second ends.

According to one embodiment of the invention, the sheath can be split into two parts that can be separated by sliding them in two opposite directions relative to the tape, the device comprising a splittable means between the two central and adjacent ends of the sheath.

According to another embodiment of the device according to the invention, the device comprises a filament arranged roughly at right angles to the longitudinal axis of the sheath, configured to cut the sheath when traction is exerted on the filament.

According to one embodiment of the device according to the invention, the sheath is made of a fluoropolymer-based heat-shrinkable material.

According to one embodiment of the device according to the invention, the tape is formed from a macroporous knitted material.

According to one embodiment of the invention, the tape in its central region has a resorbable hydrophilic film reducing the risk of adhesion to or the risk of erosion of the urethra.

According to one embodiment of the device according to the invention, the puncturing needle has a curved part continuously adjacent to a roughly straight part ending in its proximal end.

According to one embodiment of the invention, the intermediate traction element is a traction lace.

According to one embodiment, the device according to the invention comprises an end piece onto which the sheath is heat shrunk and to which the traction lace attaches.

According to one embodiment according to the invention, the traction lace has a length roughly equal to the length of the flexible means.

According to a preferred embodiment of the device according to the invention, the intermediate traction element is tubular.

According to one embodiment of the device according to the invention, the intermediate traction element and the puncturing needle are assembled by screwing.

According to one embodiment of the device according to the invention, the traction element consists of two parts of roughly the same length, placed end to end and joined together removably, for example by screwing, using a coupling.

According to one embodiment of the device according to the invention, the puncturing needle with an active distal end and a proximal end attached to a flexible and elongate means is the only puncturing needle.

BRIEF DESCRIPTION OF THE DRAWINGS

Other features and advantages of the invention will become apparent from the detailed non-limiting description given hereinafter with reference to the appended drawings, in which:

FIG. 1 depicts a view in section of the flexible means of the device according to the invention;

FIG. 2 depicts a view from above, with partial cutaway, of the flexible means shown in FIG. 1;

FIG. 3 depicts, in part, another exemplary embodiment of the flexible means of FIG. 2;

FIG. 4 depicts a partial view of a device according to the invention;

FIGS. 5 and 6 depict details of FIG. 4;

FIGS. 7 and 8 depict another embodiment of the flexible means of the device according to the invention;

FIG. 9 depicts a partial view of another embodiment of the device according to the invention;

DETAILED DESCRIPTION OF PREFERRED EMBODIMENTS

Figure 10:
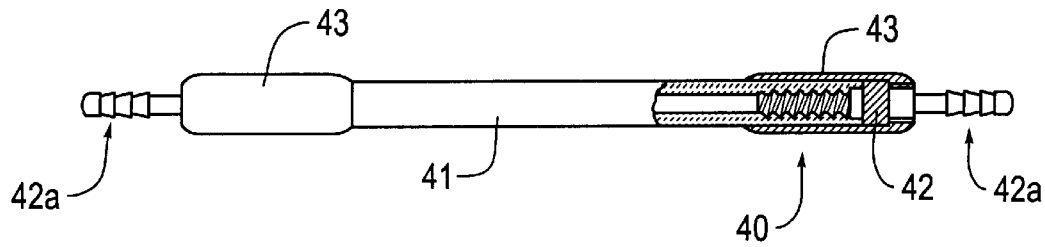
FIGS. 10, 11a, 11b and 11c depict details of the device depicted in FIG. 9.

The device depicted in FIGS. 1, 2, 3 and 4 comprises an elongate flexible means 1 generally comprising a composite band.

The flexible means 1 is shown only in part and not in its entire length. It generally has a flattened and elongate shape.

The first end 1a of the flexible means 1 can be connected to an intermediate traction element 2 (cf. FIG. 4) and the second end 1b is free or extended by an additional intermediate traction element (not depicted).

The device according to the invention also comprises a puncturing needle 3, for example made of stainless steel, connected to the intermediate traction element.

The flexible means 1 comprises a protective sheath 5 lying flat and enveloping a tape 6.

The single puncturing needle 3 has an active distal end 3a and a proximal end 3b connected to the first end 1a of the flexible means 1.

The proximal end 3b of the puncturing needle 3 is connected to the first end 1 a by virtue of an intermediate traction element 2. The proximal end 3b is thus a non-puncturing end. The proximal end 3b of the puncturing needle may have a substantially rectangular cross-section and may be flattened and/or ribbed. These features allow the surgeon to grip the needle and allows the needle to be oriented correctly.

The distal end 3a is at the end of a curved part continuously adjacent to a roughly straight part, approximately between points 3b and 3d, ending in the proximal end 3b. The distal end 3a may be partially curved and preferably has a round cross-section. Distal end 3a may have a diameter of, for example, 0.5 mm. The roughly straight part may be, for example, 20 to 25 cm in length and may, in embodiments, be ribbed over at least a portion thereof.

The puncturing needle has, for example, a diameter of 3.5 mm in its curved part.

The proximal end 3b is also equipped with an attachment means allowing it to make a connection with the intermediate traction element.

The intermediate traction element is constituted by a hollow PVC tube with a diameter that is identical to, or closely similar in diameter to, that of the needle. The intermediate traction element or tubing may be approximately 40 to 50 cm long. Its distal end 19 and proximal end 20 comprise a male screw connecting piece. This screw connecting piece is integrally fixed to the traction element by adhesion and/or screwing. The intermediate traction element may be colored, for example blue, so that it can readily be located during cystoscopy in the event of a vesical puncture.

The protective sheath 5 completely envelopes the tape 6, including its first end 6a and its second end 6b.

The sheath 5 is made, for example, of a fluoropolymer-based heat-shrinkable material. The material of which the sheath 5 is made is chosen so that it is impervious, for example hermetically sealed, to isolate the tape 6 intended to be implanted in the body of the patient from contact with the skin and mucosa when following the implantation paths through the body.

The sheath 5 may also exhibit properties of low coefficient of friction. These properties are therefore found both on the inside and on the outside of the sheath 5, so as, on the one hand, to ensure good separation from the tape 6 and, on the other hand, to reduce the friction inside the body of the patient when the flexible means 1 is being pulled.

The tape 6 advantageously has a width of between 6 and 14 mm, preferably between 10 and 12 mm and a length of between 30 and 50 cm, preferably around 40 cm.

The tape 6 is preferably formed from a macroporous knitted material.

The macroporous knitted material comprises, for example, an open knit made of single stranded polypropylene of between 0.12 and 0.16 millimeter thick and made up of two layers formed by two threaded guide bars each—one full guide and one empty guide—these two guides being moved symmetrically for open mesh according to the following chart:

bar I: 01-12-32 bar II: 32-21-01.

The tape 6 is cut to length in the warp direction of the knit. The tape 6, with a width of for example 12 mm, has the following properties:

a breaking strength in the warp direction of 105N±20%,
an elongation at break in the warp direction of 92%±20%
an elongation of 36% under a force of 20N
an onset of curling with a force of 6N and an elongation of 15%.

The expression "curling" is intended to mean the property whereby the tape 6 rolls up on itself spontaneously about its longitudinal axis under longitudinal tensile stress.

The tape 6 has attractive advantages and, in particular, low emission of particles as it is stretched, and curling which occurs only under high stress (6N). None of these aforementioned properties in any way detracts from the porosity of the tape 6.

Tape 6 can have a resorbable hydrophilic film in its central portion that reduces the risk of erosion or sclerosis of the urethra to a minimum. This central zone may be indicated by a colored marker.

In a variation, the tape may comprise other biologically acceptable materials.

The sheath 5 can preferably be split into two parts 51, 52 that can be separated by sliding them in two opposite directions with respect to the tape 6.

For this purpose, the device according to the invention has a splittable means 15, roughly at the middle of the sheath 5 and the two ends of which are secured to the corresponding and adjacent central ends 5c, 5d of the sheath 5.

The material of the splittable means 15 is chosen from materials of the thermoplastic type approved for surgical application.

The connection between, on the one hand, the central ends 5c, 5d of the two parts 51 and 52 respectively and, on the other hand, the splittable center 15, may be obtained by any means able to make the sheath 5 impervious. The same is true of the free end 5b of the sheath 5, which may be plugged and/or sealed.

The splittable means 15 comprises a flat slit 15a passing through it from one longitudinal end to the other, for the free passage of the tape 6.

The splittable means 15 may be replaced in an embodiment depicted in FIGS. 7 and 8, by an adhesive sleeve 16a joining the ends of the two splittable parts 51 and 52 of the sheath 5. This sleeve may be weakened, for example by a partial broken cut or a line of weakness in the sheath 5. The adhesive sleeve 16a made of a flexible material which sticks firmly to the central ends 5c, 5d and has a precut tab 16b to make the sleeve 16a easier to tear and therefore make the sheath 5 easier to split into the two parts 51 and 52.

According to another embodiment of the device according to the invention, the one-piece sheath 5 incorporates a filament 16c arranged roughly at right angles to the longitudinal axis of the sheath 5, configured to cut the sheath 5 when traction is exerted on the filament 16c. An example such as this is depicted, for example, in FIG. 3. The filament 16c may be advantageously in color so that it can easily be identified.

The sheath 5 can thus be split in the central zone 1c of the flexible means 1 so as to release the tape 6 inside the body of the patient.

The intermediate traction element is, according to one embodiment of the invention, configured, for example, with a traction lace 2 depicted in FIG. 4.

The device according to the invention may also comprise an end piece 4 to which the sheath 5 is attached by heat-shrinking. The sheath 5, more particularly its first end 5a, may be heat shrunk in a sealed manner onto the end piece 4.

As depicted in FIG. 2, the end piece 4 comprises anchoring notches 4a into which the heat-shrunk material of the sheath 5 engages. The end piece 4 is made, for example, of a piece of stainless steel or any other rigid material capable of contacting with intracorporal tissue.

Advantageously, the flexible means 1 comprises a knotting eye 4b (cf. FIG. 4) arranged on the outside of the sheath 5. Knotting eye 4b consists, for example, of a closed loop and may, as appropriate, have a point 4c intended to pass through and catch on one end of the traction lace 2 or any other intermediate traction element.

The knotting eye 4b may, for example, be made integrally in the end piece 4. The latter may also have a roughly flattened and partially frustoconical shape so as to achieve continuity between the various thicknesses of the traction lace 2 and the flexible means 1. The latter has a greater width than the traction lace 2. Thus a certain continuity between the dimensions of the traction lace 2 and of the flexible means 1 is obtained. The traction lace may for example be made of a Teflon-coated material.

FIG. 4 diagrammatically depicts one exemplary embodiment of the device according to the invention.

The needle 3 comprises the proximal end 3b onto which the first end 2a of the traction lace 2 is attached. The latter has, for example, at each of its ends 2a and 2b, a loop 2c (cf. FIGS. 5 and 6 respectively) obtained by ultrasonic welding, stitching or any other means.

One of these loops, 2c, is mounted on the proximal end 3b of the needle 3 while the other is mounted in the eye 4b.

During the procedure, it is thus possible to attach the end 2a of the traction lace 2 to the eye 4b either using the point 4c secured to the eye 4b or simply by running it through the closed loop that forms the eye 4b.

The device according to the invention therefore, for example, has a traction lace 2, the length of which is, for example, roughly equal to the length of the flexible means 1, namely a length of between 30 and 60 cm, for example 40 cm. Such dimensions or lengths of the traction lace 2 make it possible, if reference is made to the operative procedure, to avoid engaging the flexible means 1 in the body before being sure that the path taken by the needle 3 and the traction lace 2 is optimum. The long available length of traction lace 2 for carrying out the operative actions described thus makes it possible for another path to be taken through the body if need be, without having to manipulate the flexible means 1.

By way of variation, it is possible to provide the second end 1b of the flexible means 1 with an additional intermediate traction element, such as an additional lace like the one previously described under reference 2.

An additional traction lace 2 secured to the free end 1b, which may also have an end piece 4 for this purpose, allows traction to be exerted in the opposite direction to its introduction on the flexible means 1, and allows it to back-track along its path if it is penetrating incorrectly.

According to another embodiment of the device according to the invention, depicted for example in FIG. 9, the intermediate traction element is a tubular element 20. The material of which the latter is made may be, for example, PVC. Tubular element 20 may be, for example, 2.5 mm in diameter.

The tubular element 20 is preferably semirigid, so that it can be screwed onto a threaded end 3c secured to the proximal end 3b of the needle 3. The other end of the tubular element 20 is connected, for example by screwing, to the flexible means 1 comprising an end piece 30 secured to the sheath 5, for example by heat shrinking. The end piece 30 for this purpose has a complementary threaded part 30a (see FIGS. 7 and 8).

The flexible means 1, the tubular element 20 and the two parts 3a, 3b of the puncturing needle 3 may thus be assembled removably by screw fastening.

Other known removable means of connection or attachment may also be suitable in the context of the present invention.

The tubular element consists for example of a number of parts of roughly the same length, for example 20 and 41, placed end to end and joined together removably by screw fastening. This end-to-end joining is obtained using a coupling 40 depicted in FIGS. 10, 11a, 11b and 11c.

The coupling 40 is made up of two elements, namely an internal connecting mandrel 42 and an external clamping bush 43.

Figure 11A:
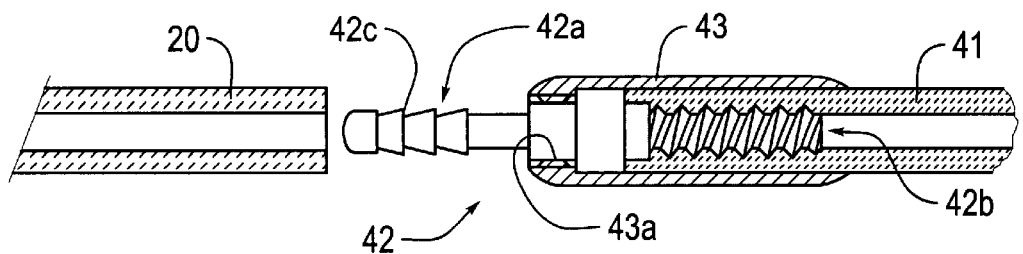
Figure 11B:
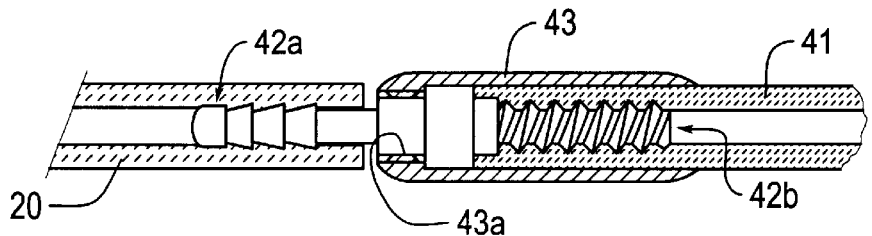
Figure 11C:
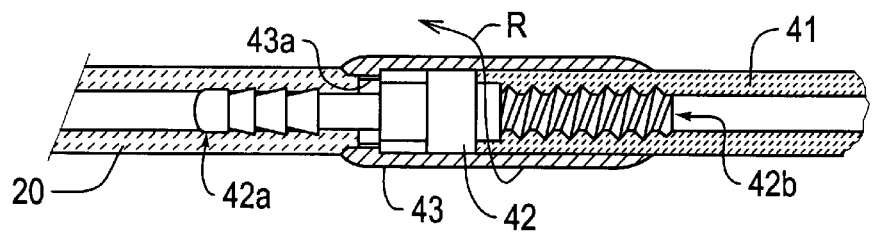

At one end, the mandrel 42 has a threaded nipple 42b engaged in the tubular element part 41 and at the other end has a stud 42a with teeth 42c intended to be engaged in the tubular element part 20 as depicted in FIGS. 11b and 11c. The shape and dimensions of the teeth 42c tend to oppose separation of the tubular element part 20 from the mandrel 42.

Each mandrel 42 is associated with a bush 43 engaged on the tubular element part 41 so as to clamp part of tubular element part 41 between the threaded nipple 42b and bush 43.

Bush 43 may also be provided on the anterior end with a tapping 43a which bites by screwing into the material of which the abutting end of part 20 is made.

To begin with, one end of part 41 of the tubular element is screwed onto the nipple 42b. Bush 43 is then attached to this end of the part 41, with the constituent material trapped between the screw thread of the nipple 42b and the sleeve 43, the latter also clamping the rest of the mandrel 42 except for the projecting stud 42a.

The two tubular element parts 20 and 41 are assembled by engaging the stud 42a in one end of part 20 (FIG. 11b) and then by screwing the end of bush 43 onto the exterior periphery of part 20 (FIG. 11c). The turning of bush 43 is depicted diagrammatically by the arrow R in FIG. 11c. The mechanical connection between the tubular element part 20 and the coupling 40 is thus improved.

The device according to the present invention makes it possible to implement a method for treating women suffering from urinary stress incontinence. This method will be specified herein below and allows the tape 6 to be fitted in the patient's body.

The treatment method comprises:

a) forming an opening 103a in the anterior vaginal wall 103;

b) making two small suprapubic incisions 106, 107;

c) using the puncturing needle 3 connected to an intermediate traction means 2 or 20 to create a first path traveling around the pubic bone 105 and emerging in the opening 103a formed in the anterior vaginal wall 103;

d) using the puncturing needle 3 connected to an intermediate traction means to create a second path around the pubic bone 105 and emerging in the opening 103a formed in the anterior vaginal wall 103;

e) using cystoscopy to check that the making of these paths has not punctured the bladder 101 or the urethra 100;

f) connecting the parts of the device emerging from the opening 103a formed in the anterior vaginal wall 103;

g) pulling on the intermediate traction element 2 or 20 to adjust the loop formed by the flexible means 1 on the underside of the urethra 100;

h) separating and withdrawing the two halves of the sheath 5; and i) leaving the tape 6 between the first suprapubic incision 106 and the second suprapubic incision 107 passing under the underside of the urethra 100.

According to one embodiment of the invention, the method comprises guiding the paths of the puncturing needle 3 along the posterior surface 105a of the pubis, by contact with the finger 50 of the surgeon introduced through the opening 103a, formed in the anterior vaginal wall 103, as far as the lower edge 105b of the same side of the pubis 105.

In a variation, a one-piece needle may be used that can terminate in a male screw connecting piece. Passage of a track on the right and left side is made by screwing a portion of the traction element to the proximal end of the needle. Cystoscopy verifies the absence of punctures; then the two tubular halves are connected to each other using the small metal part to form a single traction element disposed in a loop beneath the urethra. The remainder of the intervention is identical.

According to one embodiment of the method according to the invention, the flexible means 1 is attached to the intermediate element 2 or 20 after the check provided for in step (e) has been made.

According to one embodiment of the method according to the invention, the opening 103a made in the anterior vaginal wall 103 is vertical.

According to a method of the invention, a urethral probe 60, for example of the FOLEY balloon type, may be inserted into the patient beforehand.

According to one embodiment of the treatment method according to the invention, use is made of two intermediate traction elements 2 or 20 connected end to end during step (f).

According to another embodiment of the treatment method according to the invention, the puncturing needle 3 and the intermediate traction element 2 or 20 are separated once the check according to step (e) has been made and once the flexible means 1 has been introduced along the first path. This separation then makes it possible to create the second path using the puncturing needle 3 connected to the intermediate traction element 2 or 20.

All of the above defined steps are now described with a device according to FIGS. 7 to 11 and the description relating thereto.

Figure 13:
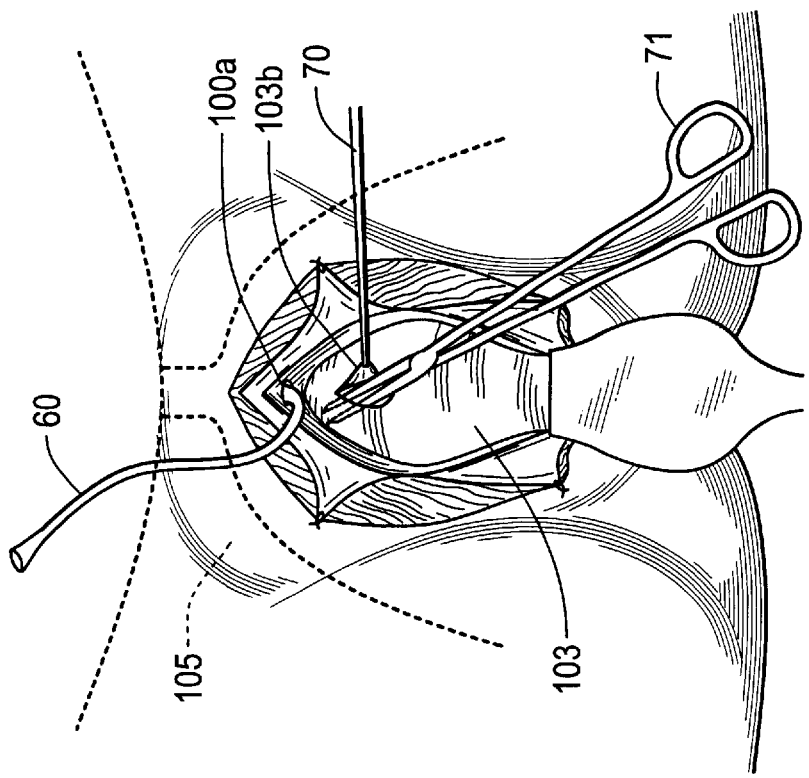
FIGS. 12 to 19 diagrammatically depict the surgical method employed using the device according to the invention.
Figure 12:
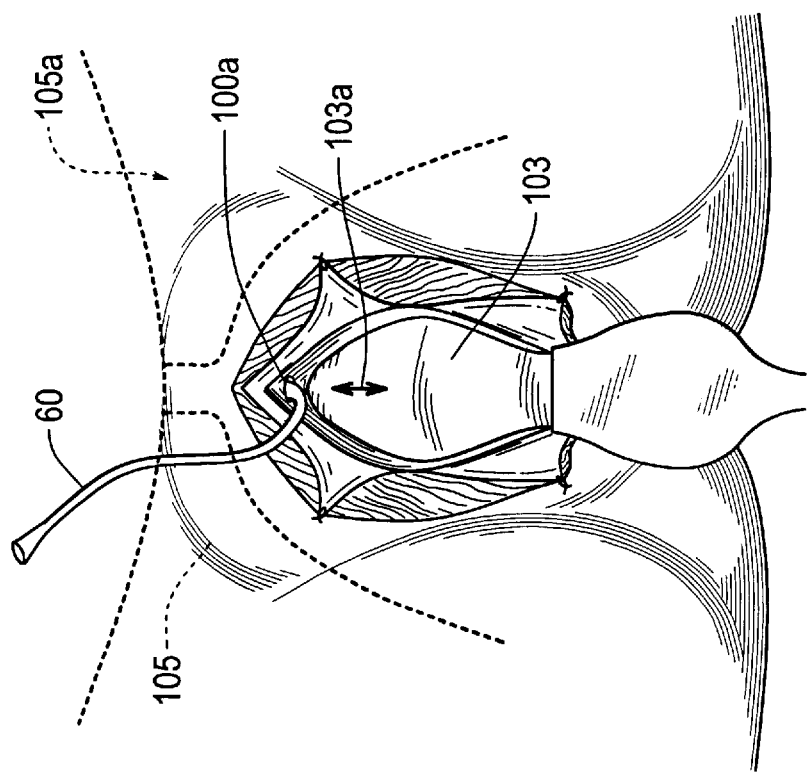

The first step (a) is illustrated in FIG. 12. The patient is placed in a gynecological position and a sterile operating zone is formed. A urethral balloon probe 60 is positioned in the bladder 101 and is connected to a sterile collecting bag to empty and flatten the bladder 101. A short vertical incision 103a, at most 30 mm long, is made in the middle of the vaginal wall 103, for example in a T or I shape, centered in the central third of the urethral canal 100 opening to the urinary meatus 100a. Each lip 103b of the vaginal incision 103a is detached from the underlying tissues using scissors 71 and appropriate instruments 70, as illustrated in FIG. 13.

Figure 14:
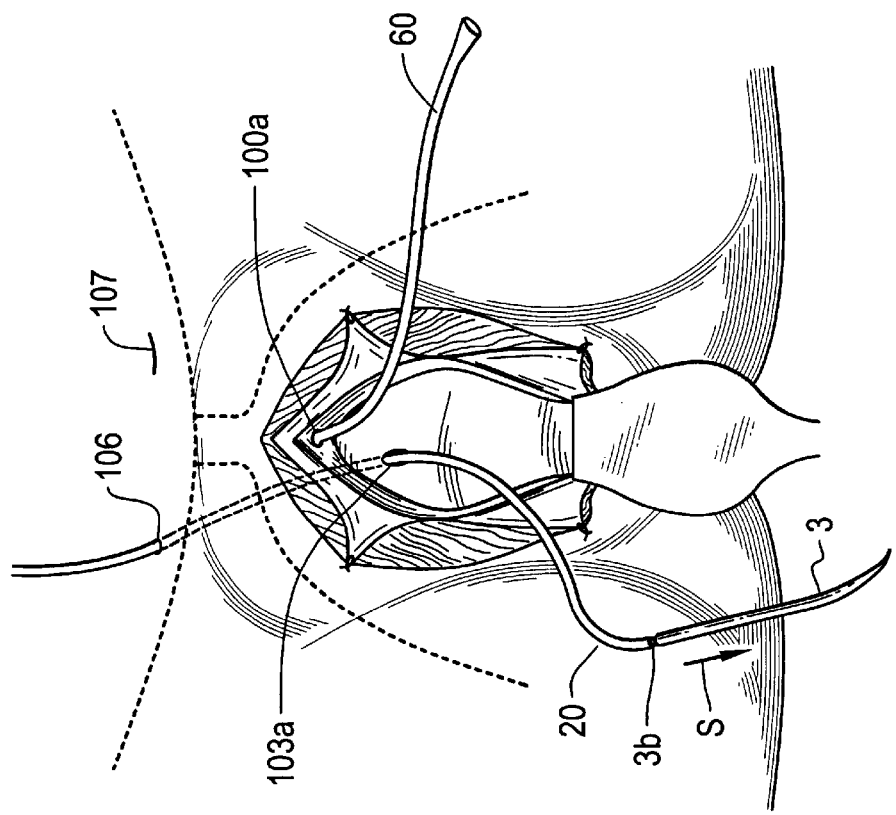

Detachment is performed until the surgeon's index finger 50, introduced through the resulting opening 103a, can reach the lower edge 105b of the pubis 105, away from the urethra 100 and the periurethral tissue (FIG. 14).

Next, a very small cutaneous incision 106, 107 less than 10 mm long is made in the abdominal skin immediately above the pubis 105, on each side of the centerline and about 20 mm away from the latter, to allow the percutaneous passage of the needle 3 just off the posterior face 105a of the pubis 30 in the direction of the vagina 104.

The surgeon's index finger 50 is introduced into the vaginal passage thus prepared by detachment, and the active distal end 3a of the needle 3 follows a path to come into direct contact with index finger 50. The path of the puncturing needle 3 is therefore controlled. The needle 3 can then reemerge through the vaginal opening 103a and the bladder 101 has remained safe from any injury by the needle.

Figure 15:
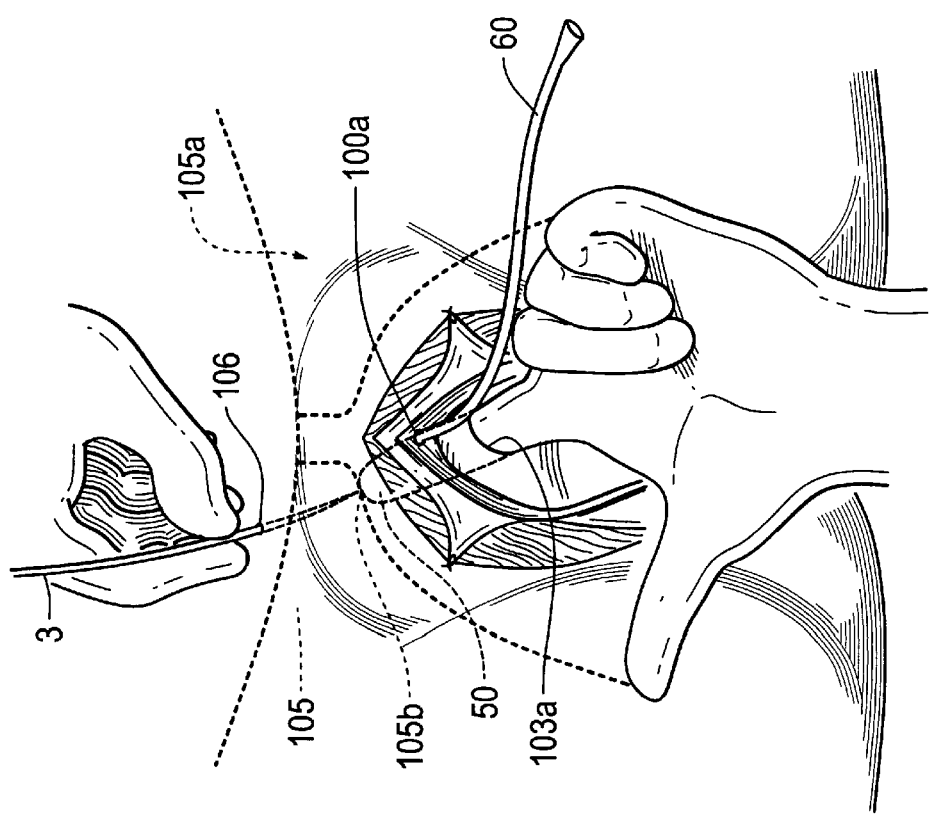

In general, the straight percutaneous path is made first. The end of the intermediate traction element, for example the tubular element 20, reemerges behind the needle 3 via the vaginal opening 103a. This end of the traction element 20 is for example unscrewed from the proximal end 3b of the needle 3 and is detached from the latter in the direction of the arrow S in FIG. 15.

Figure 16:
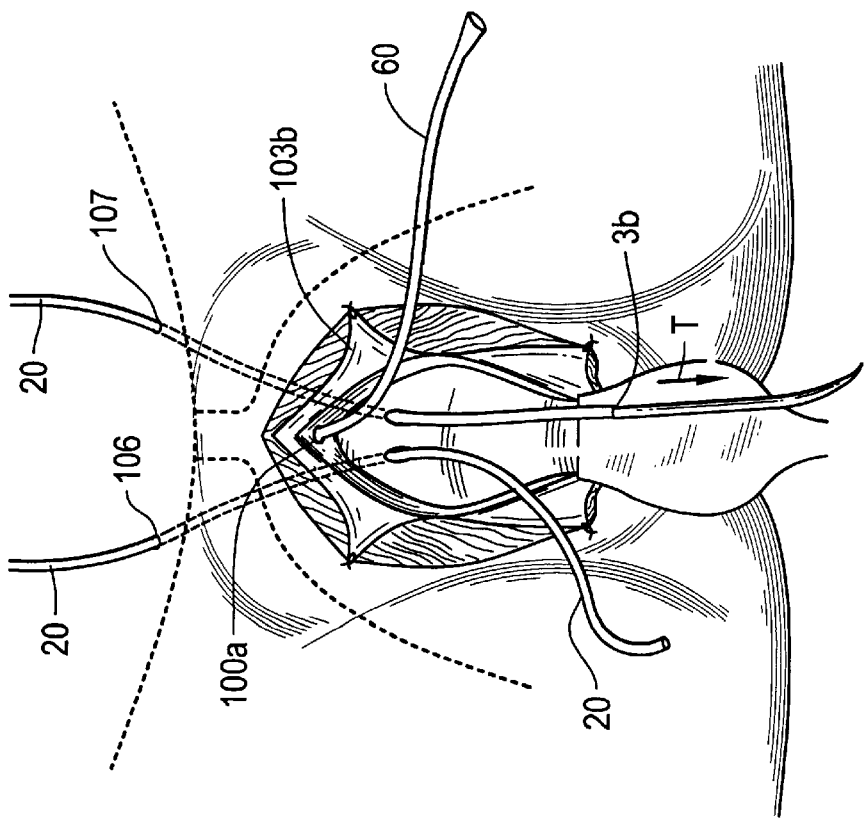

The needle 3 is then passed along the second path (on the left-hand side in FIG. 16) in the same way as for the first side (right-hand side). Once the distal part 3a of the needle is well away from the vaginal opening 103a, it can be detached by unscrewing its proximal portion 3b. This separation is depicted diagrammatically by the arrow T in FIG. 16.

The so-called proximal portion 3b is long enough to project when the percutaneous incision 107 is made.

By way of an alternative form according to the invention, the proximal portion 3b may be extended by an additional tubular element 20 which projects out of the abdominal incision 107.

The next step consists in connecting the end of the tubular traction element 20 that follows the first path to the proximal portion 3b or to the additional tubular element 20 that follows the second path.

Figure 17:
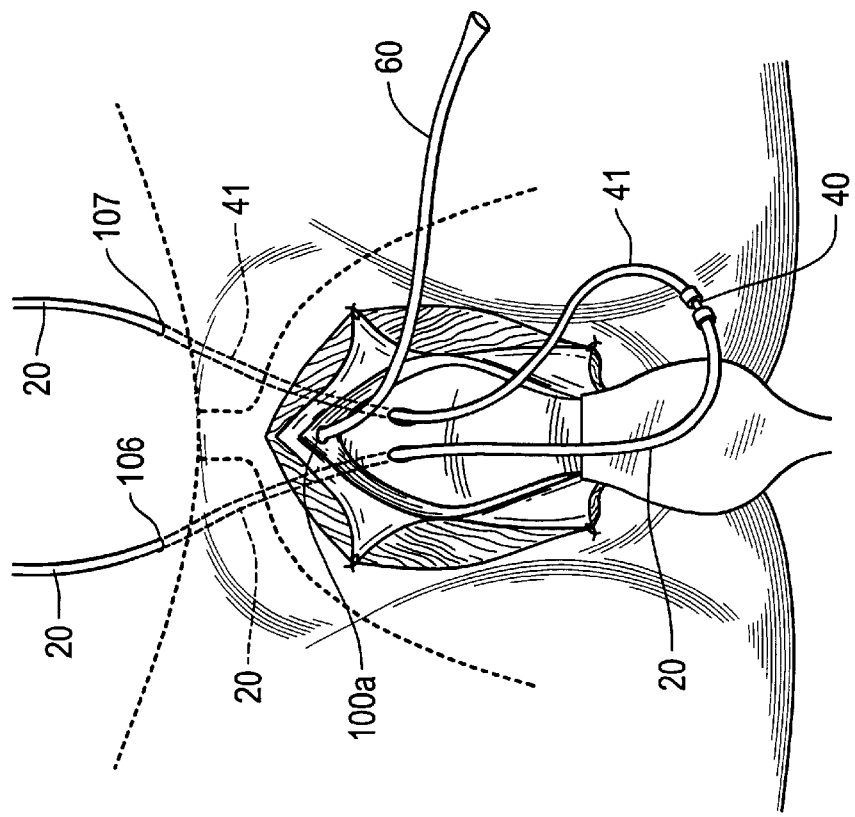

Connection is made using the coupling 40 depicted in FIG. 17.

Figure 18:
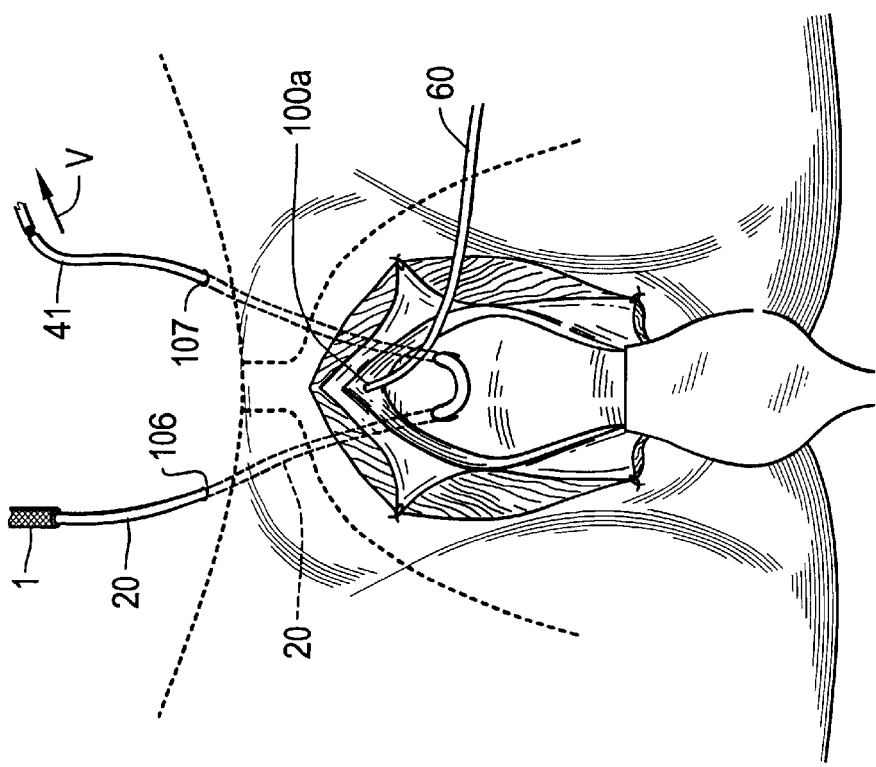

The proximal portion 3b is then led back out through the abdomen by pulling in the direction of the arrow V illustrated in FIG. 18.

Before the flexible means 1 penetrates the patient's body, the tubular element 20 thus forms a loop around the urethra and its two ends reemerge respectively through the two abdominal cutaneous incisions 106 and 107 (FIG. 18).

The urethral probe 60 may then be removed and cystoscopy is used to check for the absence of vesical perforation.

Figure 21:
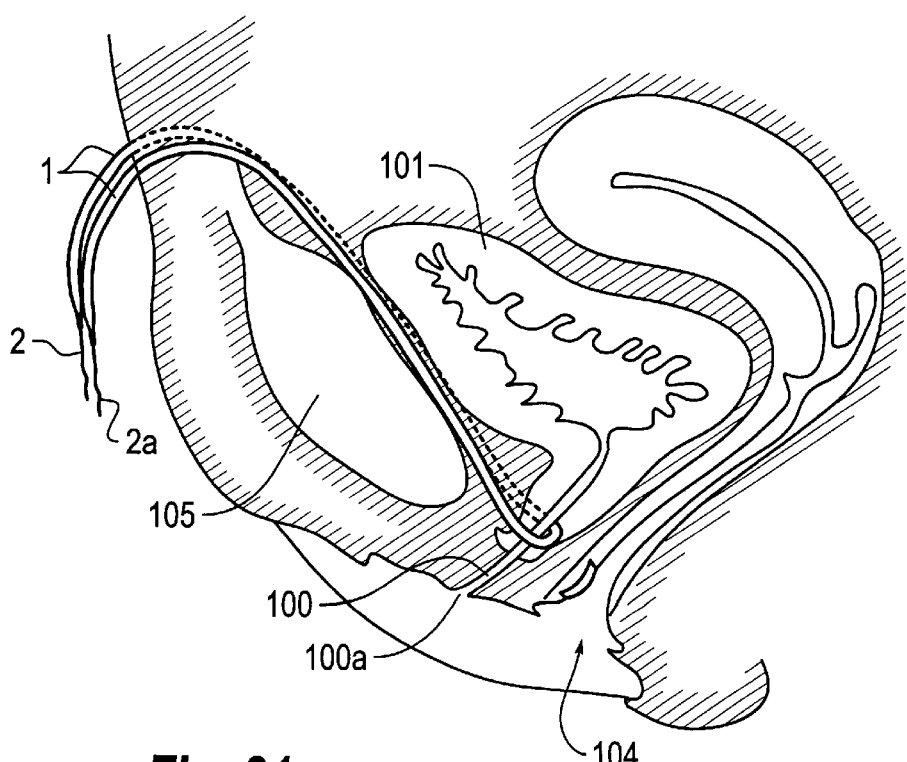

Once the check has been made, the end of the tubular element 20 that emerges from the abdominal incision 106 is assembled by screw fastening on the threaded end 30a of the flexible means 1 (sheath 5 plus tape 6) and the assembly is pulled (arrow V in FIG. 18) through the right and left paths to position the flexible means 1 under the urethra 100. When this positioning which corresponds to step (g) is complete, the ends 1a, 1b of the flexible means 1 reemerge from the abdominal incisions 106, 107 as depicted in FIG. 21.

Figure 19:
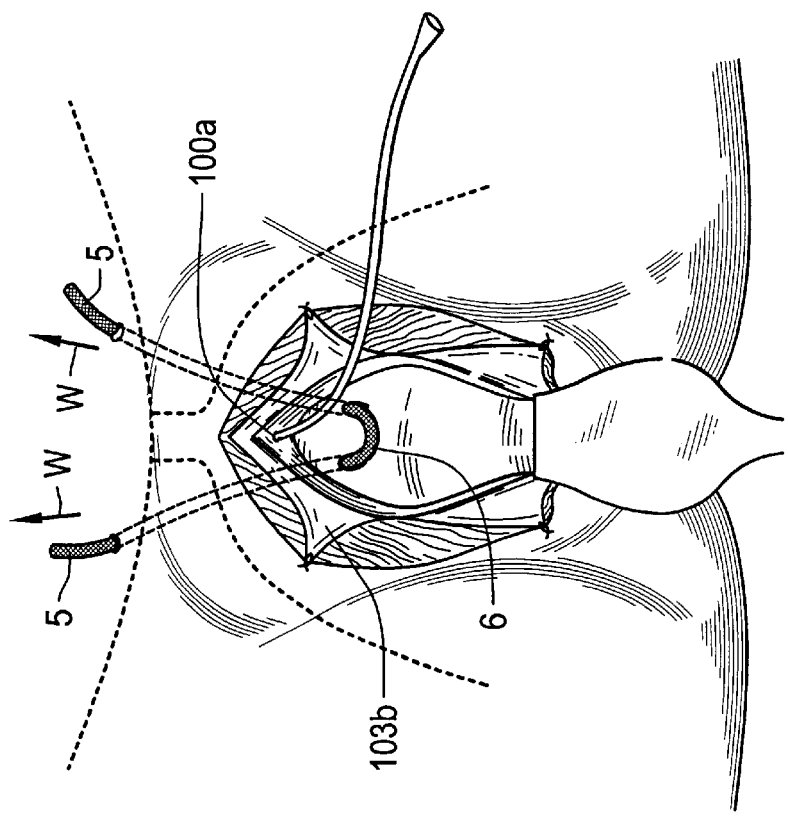

The sheath 5 may then be separated from the tape 6 by cutting the sheath 5 in its central zone Ic and withdrawing each of the halves 51 and 52 thus obtained through the corresponding abdominal incision 106, 107 according to step (h) (arrows W in FIG. 19).

Figure 20:
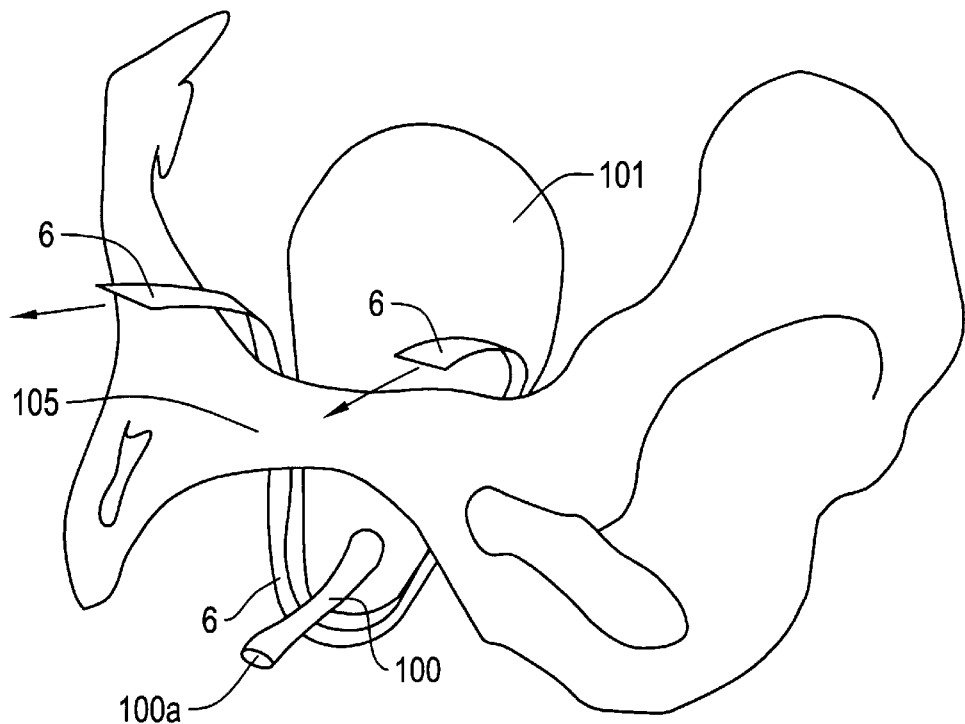
FIGS. 20 and 21 diagrammatically depict the position of the device according to the invention in the body of a patient.

The tape 6 may thus be released, positioned and adjusted under the underside of the urethra 100, usually in a central position, without tension and without being squashed, as depicted in FIG. 20.

Once the sheath 5 has been withdrawn through each abdominal incision 106 and 107, the parts of the tape 6 which project out of the incisions 106 and 107 are cut off flush with the abdominal wall, the parts being left at the subcutaneous site.

The cutaneous incisions may be closed up using conventional methods.

The tape 6 advantageously runs around the pubic bone 105 via its pelvic or deep face, and heads towards the contralateral abdominal wall.

The resulting vaginal incision 103a made in the vaginal wall 103 may then be closed once the definitive position of the tape 6 under the urethra 100 has been checked.

By way of a variation, the traction lace 2 can also be used for implementing the method.

The operating procedure thus used is notable in that it is a percutaneous operating technique because the dimension of the abdominal cutaneous incisions is minimal, intended to be just enough to allow the needles to pass through and because the paths taken by the needle 3 are downwards, in other words entering through abdominal incisions 106 and 107 to emerge through the predetermined and prepared corresponding vaginal opening 103a.

This presents an enormous advantage from the safety point of view with respect to the risks of puncturing the bladder 101 on the one hand, and the iliac vessels on the other hand.

This is a considerable advantage over the known operating technique. The path can be checked by cystoscopy.

When it becomes apparent that the path is not appropriate, it is possible to withdraw the intermediate traction element 2 or 20 to make a second path through the abdominal cutaneous incision 106, and to do so without introducing the flexible means 1 into the body.

All of the elements of the device according to the invention can thus be reused if the manipulation is incorrect, or if the path inside the patient's body needs to be improved or optimized. This represents a considerable advantage over the state of the prior art.

Furthermore, the surgical technique described requires neither the use of an insertion tool for the needle, nor the use of an endovesical rod to move the bladder 101 and the urethra 100 away each time the needle 3 passes on a downward path. This constitutes an advantageous simplification insofar as the surgical technique put forward in the state of the art entails the use of an endovesical rod twice, namely after each passage of each of the two needles which are making an upward path.

It is to be noted that the device according to the invention is a percutaneous device, which is advantageous when compared with the known device which enters via the vaginal mucosa and emerges through the skin in the abdominal suprapubic region.

It is notable that the extreme simplicity of the device according to the invention contributes not only to reducing its cost price and the number of its constituent parts but also to increasing the safety for the patient and the quality of the result when the operating technique described in the present invention is implemented.

Checking the effect obtained on continence and adjusting the tension of the tape 6 are not justified for two main reasons. Specifically, continence in a lying-down position is not comparable to the upright position, and the effectiveness of the tape is explained not by a gripping effect (which carries the risk of leading to stenosis) but by an effect of providing uplifting support.

Furthermore, the operator chooses the position of the tape 6 with respect to the urethral duct 100 according to the clinical case being studied.

In the state of the art, this choice cannot be made, and continence tests are carried out after the bladder has been filled and coughing stress applied in order to adjust the tension in the tape, even though the technique is supposedly said to be "tension free".

What is claimed is:

1. A device for treating urinary stress incontinence in women, comprising:
    a flexible and elongate mechanism comprising a tape for supporting a urethra and a flat protective sheath enveloping said tape; and
    a puncturing needle with an active distal end and a proximal end connected to a first end of the flexible and elongate mechanism,
wherein the proximal end of the puncturing needle is connected to a first end of the flexible and elongate mechanism by an intermediate traction element, a second end of the flexible and elongate mechanism being free.

2. The device of claim 1, wherein the free second end of the flexible and elongate mechanism is attached to an extended by an additional intermediate traction element.

3. The device of claim 1, wherein the tape has a first end and a second end and wherein the protective sheath completely envelopes the tape, including said first and second ends of the tape.

4. The device of claim 1, wherein the sheath is capable of being split into two parts that are separable by sliding them in opposite directions relative to the tape, and wherein said device comprises a splittable mechanism between central and adjacent ends of the sheath.

5. The device of claim 1, wherein the sheath is capable of being split into two parts that are separable by sliding them in opposite directions relative to the tape, and wherein said device comprises a filament arranged roughly at right angles to a longitudinal axis of the sheath, wherein said filament is configured to cut said sheath when traction is exerted on said filament.

6. The device of claim 1, wherein the sheath comprises a fluoropolymer-based heat-shrinkable material.

7. The device of claim 1, wherein the tape comprises a macroporous knitted material.

8. The device of claim 1, wherein a central region of the tape has a resorbable hydrophilic film that reduces the risk of adhesion to or the risk of erosion of the urethra.

9. The device of claim 1, wherein the puncturing needle has a curved part adjacent to a roughly straight part that ends at the proximal end of the puncturing needle.

10. The device of claim 9, wherein the traction lace has a length roughly equal to the length of the flexible and elongate mechanism.

11. The device of claim 10, wherein the tubular traction element and the puncturing needle are attached by screwing them together.

12. The device of claim 10, wherein the tubular traction element comprises two parts of roughly equal length, placed end to end and joined together removably.

13. The device of claim 12, wherein said two parts of roughly equal length are joined together by screwing them together using a coupling.

14. The device of claim 1, wherein the intermediate traction element is a traction lace.

15. The device of claim 14, wherein said device further comprises an end piece onto which the sheath is heat shrunk and to which the traction lace attaches.

16. The device of claim 1, wherein the intermediate traction element is a tubular traction element.

17. The device of claim 1, wherein the puncturing needle with an active distal end and a proximal end connected to a first end of the flexible and elongate mechanism is the only puncturing needle present in the device.

18. The device of claim 1, wherein the tape comprises an open knit made up of two layers formed by two threaded guide bars each, one full guide and one empty guide, the two threaded guide bars being movable symmetrically for an open mesh.

19. A method for treating urinary stress incontinence in a woman suffering from urinary stress incontinence, said method comprising:

(a) forming an opening in an anterior vaginal wall;
(b) creating, from two small suprapubic incisions formed in the abdominal wall, a right track and a left track from the abdominal skin to the opening formed in the anterior vaginal wall;
(c) using a needle and an intermediate traction element to follow one of the tracks from one said small suprapubic incision to the opening formed in the anterior vaginal wall and following the other track with at least a needle;
(d) verifying by cystoscopy that the paths of the tracks are outside the bladder and the urethra;
(e) using a support tape surrounded by a plastic sheath to follow the tracks by passage under an inferior surface of the urethra;
(f) adjusting a loop formed by the sheathed tape under the inferior surface of the urethra;
(g) removing the sheath by pulling the sheath toward the outside of the woman's body through the small suprapubic incisions; and
(h) leaving the support tape implanted from the first to the second incision and around the urethra to support the urethra.

20. The method of claim 19, wherein the needle and the intermediate traction element are used to follow one of the tracks, and a needle and a second intermediate traction element are used to follow the other track.

21. The method of claim 19, wherein each track is produced using a needle inserted through a suprapubic incision and guided along a posterior surface of a pubis in contact with a finger of a surgeon and introduced through an opening to a lower rim of the pubis on the same side as the suprapubic incision through which the needle was inserted.

22. The method of claim 19, wherein a distal end of the tape is connected to a proximal end of the intermediate traction element after verifying by cystoscopy.

23. The method of claim 19, wherein the sheath is cut in a central region.

24. The method of claim 19, wherein the incision in the anterior vaginal wall is T or I shaped.

25. The method of claim 19, in which vaginal detachment is performed.

26. The method of claim 19, in which a urethral probe is inserted prior to performing a first incision.

27. A method for treating urinary stress incontinence in a woman suffering from urinary stress incontinence, said method comprising:
(a) forming an opening in an anterior vaginal wall;
(b) creating, from two small suprapubic incisions formed in the abdominal wall, a right track and a left track from the abdominal skin to the opening formed in the anterior vaginal wall;
(c) using a needle and an intermediate traction element to follow one of the tracks from one said small suprapubic incision to the opening formed in the interior vaginal wall and following the other track with at least a needle;
(d) using a support tape to follow the tracks; and
(e) leaving the support tape implanted from the first to the second incision and around the urethra to support the urethra.

* * * * *